United States Patent
Itakura et al.

(10) Patent No.: US 10,444,175 B2
(45) Date of Patent: Oct. 15, 2019

(54) MEASUREMENT DEVICE

(71) Applicant: DENSO CORPORATION, Kariya, Aichi-pref. (JP)

(72) Inventors: Keisuke Itakura, Kariya (JP); Teruaki Kaifu, Kariya (JP)

(73) Assignee: DENSO CORPORATION, Kariya (JP)

( * ) Notice: Subject to any disclaimer, the term of this patent is extended or adjusted under 35 U.S.C. 154(b) by 165 days.

(21) Appl. No.: 15/086,902

(22) Filed: Mar. 31, 2016

(65) Prior Publication Data

US 2016/0290893 A1 Oct. 6, 2016

(30) Foreign Application Priority Data

Apr. 3, 2015 (JP) .................................. 2015-077263
Sep. 16, 2015 (JP) .................................. 2015-182528

(51) Int. Cl.
*G01N 27/12* (2006.01)

(52) U.S. Cl.
CPC .................................. *G01N 27/121* (2013.01)

(58) Field of Classification Search
None
See application file for complete search history.

(56) References Cited

U.S. PATENT DOCUMENTS

| | | | |
|---|---|---|---|
| 4,304,130 A | 12/1981 | Peter et al. | |
| 4,562,745 A * | 1/1986 | Parra | G01F 1/3245 73/861.22 |
| 6,253,606 B1 | 7/2001 | Yonezawa et al. | |
| 6,516,785 B1 | 2/2003 | Nakada et al. | |
| 6,615,655 B1 * | 9/2003 | Sakai | G01F 1/6845 73/204.26 |
| 10,030,601 B2 * | 7/2018 | Kaifu | F02D 41/18 |
| 2004/0055376 A1 * | 3/2004 | Thompson | F02D 41/18 73/204.22 |
| 2009/0038376 A1 * | 2/2009 | Petrosyan | G01N 25/56 73/25.04 |
| 2011/0088464 A1 | 4/2011 | Ariyoshi et al. | |
| 2013/0036806 A1 * | 2/2013 | Kohno | G01F 1/684 73/114.33 |
| 2015/0260672 A1 * | 9/2015 | Kaufmann | F02D 41/18 73/29.05 |

(Continued)

FOREIGN PATENT DOCUMENTS

| | | |
|---|---|---|
| JP | 5-231899 A | 9/1993 |
| JP | 9-210801 A | 8/1997 |
| JP | H10-54840 | 2/1998 |

(Continued)

*Primary Examiner* — Nimeshkumar D Patel
*Assistant Examiner* — Jean F Morello
(74) *Attorney, Agent, or Firm* — Nixon & Vanderhye, P.C.

(57) ABSTRACT

A measurement device includes a bypass housing placed at a position in the intake duct that introduces an intake air to an internal combustion engine and defining a passage through which a part of the intake air flowing through an interior of the intake duct passes, a flowing amount sensor measuring a flowing amount of the intake air passing through the interior of the bypass housing, a humidity detection element measuring a humidity of the intake air passing through a position in the vicinity of the bypass housing, and a heat discharge portion being directly in contact with the intake air and being thermally bonded to the humidity detection element.

26 Claims, 11 Drawing Sheets

(56) References Cited

U.S. PATENT DOCUMENTS

2018/0245962 A1    8/2018  Enomoto et al.

FOREIGN PATENT DOCUMENTS

| JP | 2004-228410 A | 8/2004 |
| JP | 2008-20193    | 1/2008 |
| JP | 2008-175780   | 7/2008 |
| JP | 2010-181354 A | 8/2010 |
| JP | 2013-195231 A | 9/2013 |
| JP | 5279667       | 9/2013 |
| JP | 2014-10026    | 1/2014 |
| JP | 2015-87196    | 5/2015 |

* cited by examiner

FIG. 9A
FIG. 9B
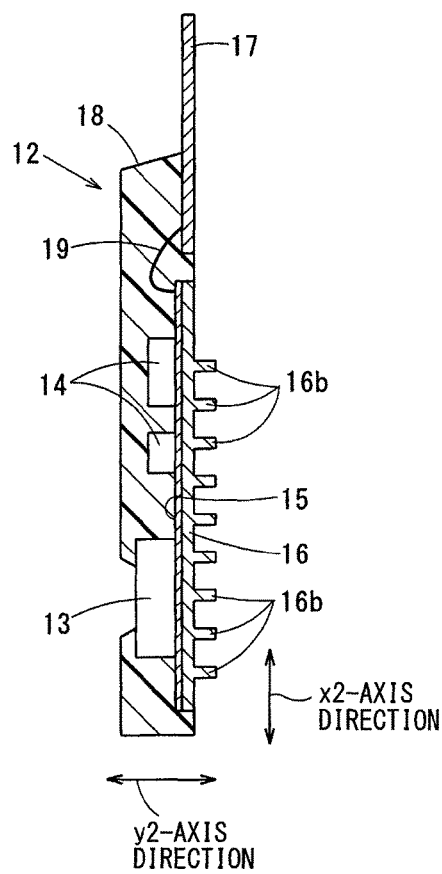
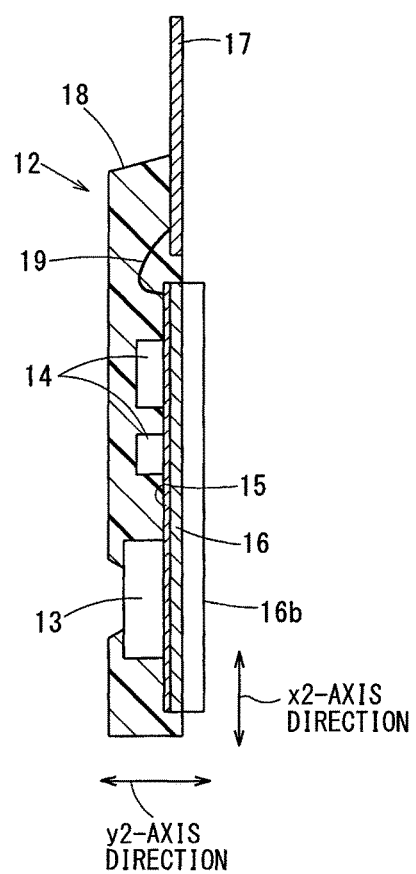

MEASUREMENT DEVICE

CROSS REFERENCE TO RELATED APPLICATION

This application is based on Japanese Patent Application No. 2015-77263 filed on Apr. 3, 2015, and Japanese Patent Application No. 2015-182528 filed on Sep. 16, 2015, the disclosure of which are incorporated herein by reference.

TECHNICAL FIELD

The present disclosure relates to a measurement device which measuring a flow and a humidity of an intake air suctioned into an internal combustion engine.

BACKGROUND

Conventionally, it is well known that a measurement device includes a flowing amount sensor and a humidity sensor which are arranged in an intake duct through which an intake air flows, so as to measure a flowing amount and a humidity of the intake air.

According to JP2015-87196A, the measurement device includes a housing that supports the flowing amount sensor and protrudes toward an inner periphery of the intake duct, and the humidity sensor is arranged on a side surface of the housing.

However, in the above measurement device, a heat of an internal combustion engine is transmitted to the humidity sensor through the housing, and a temperature of the humidity sensor is increased. Therefore, the temperature of the humidity sensor is different from a temperature of the intake air, and a bad effect to a detection value of the humidity of the intake air is generated. Thus, it is necessary to prevent a heat transmission from the housing to the humidity sensor.

According to Japanese Patent No. 5445535, it is well known that an assembly supporting the humidity sensor is provided separately from the housing, and the assembly is separated from the housing and protrudes toward the inner periphery of the intake duct.

In the above measurement device, since the housing is separated from the assembly, the heat transmission from the housing to the humidity sensor can be prevented, and an increasing of the temperature of the humidity sensor can be suppressed.

However, according to Japanese Patent No. 5445535, since the assembly has a cross section that is perpendicular to a longitudinal direction of the assembly and is a rectangle shape, a pressure loss may generate relative to a flow of the intake air.

According to Japanese Patent No. 5445535, a humidity detection element is mounted to the measurement device, and the measurement device measures the flowing amount and the humidity of the intake air.

It is highly possible that the measurement device and the intake duct provided with the measurement device receive a heat of an engine room, and then a temperature of the measurement device and a temperature of the intake duct are increased.

Then, a heat of the measurement device and the intake duct is transmitted to the humidity detection element through a member supporting the humidity detection element or a connection portion that is electrical. In this case, the member may be a bypass housing, and the connection portion may be a lead pin.

As a result, the temperature of the humidity detection element is higher than the temperature of the intake air passing through an interior of the intake duct. When the temperature of the humidity detection element is different from the temperature of the intake air that is a measurement subject, the humidity of the intake air cannot be accurately measured by the humidity detection element.

According to WO2014/060161, a cover covers the humidity sensor.

In the measurement device according to WO2014/060161, the cover includes two openings arranged along a flowing direction of the intake air. The intake air flows into the cover through the opening that is placed at a upstream side of the other opening, passes through the measurement device, and returns to the intake duct through the opening that is placed at a downstream side.

According to WO2014/060161, the measurement device prevents a foreign matter from entering the cover so as to protect the humidity sensor. However, the measurement device cannot efficiently suppress the pressure loss.

SUMMARY

It is an object of the present disclosure to provide a measurement device which can improve an accuracy of a detection of a humidity of an intake air by forcibly approaching a temperature of a humidity detection element to a temperature of the intake air, and suppresses a pressure loss generated by an assembly supporting a humidity sensor in a case where the measurement device arranged in an intake passage.

According to a first aspect of the present disclosure, the measurement device includes a bypass housing placed at a position in the intake duct that introduces an intake air to an internal combustion engine and defining a passage through which a part of the intake air flowing through an interior of the intake duct passes, a flowing amount sensor measuring a flowing amount of the intake air passing through the interior of the bypass housing, a humidity detection element measuring a humidity of the intake air passing through a position in the vicinity of the bypass housing, and a heat discharge portion being directly in contact with the intake air and being thermally bonded to the humidity detection element.

According to a second aspect of the present disclosure, the measurement device includes a flowing amount sensor measuring a flowing amount of an intake air flowing through an intake duct, a humidity sensor measuring a humidity of the intake air, a first protrusion portion supporting the flowing amount sensor and protruding toward an inner periphery of the intake duct, and a second protrusion portion supporting the humidity sensor and being a rod shape and protruding toward the inner periphery of the intake duct to be separated from the first protrusion portion. The humidity sensor is laid in a surface of the second protrusion and is supported by the second protrusion, so as to be exposed to the intake duct. The second protrusion protrudes toward the inner periphery of the intake duct such that a longitudinal direction of the second protrusion is perpendicular to a flowing direction of the intake air. When a cross section of the second protrusion that is perpendicular to the longitudinal direction is expressed as a vertical cross section, a periphery of the vertical cross section is a streamline shape relative to a flow of the intake air.

BRIEF DESCRIPTION OF THE DRAWINGS

The above and other objects, features and advantages of the present disclosure will become more apparent from the following detailed description made with reference to the accompanying drawings. In the drawings:

FIG. 9A is a cross section of the humidity sensor taken in the longitudinal direction, according to a ninth embodiment of the present disclosure;

FIG. 9B is a cross section of the humidity sensor taken in the longitudinal direction, according to the ninth embodiment;

DESCRIPTION OF EMBODIMENTS

Figure 1A:
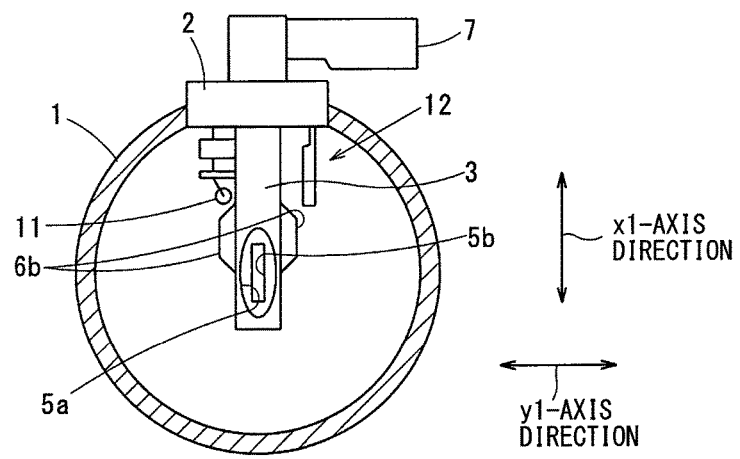
FIG. 1A is a diagram showing an outline of a measurement device viewed from an upstream in a flowing direction of an intake air, according to a first embodiment of the present disclosure.

Embodiments of the present disclosure will be described hereafter referring to drawings. In the embodiments, a part that corresponds to a matter described in a preceding embodiment may be assigned with the same reference numeral, and redundant explanation for the part may be omitted. When only a part of a configuration is described in an embodiment, another preceding embodiment may be applied to the other parts of the configuration. The parts may be combined even if it is not explicitly described that the parts can be combined. The embodiments may be partially combined even if it is not explicitly described that the embodiments can be combined, provided there is no harm in the combination.

Hereafter, embodiments of the present disclosure will be described referring to drawings. The present disclosure is not limited to the embodiments, and can be applied to various embodiments which are also within the spirit and scope of the present disclosure.

[First Embodiment]

Referring to FIGS. 1A to 2C, a first embodiment of the present disclosure will be described.

A measurement device is mounted to an intake duct 1 introducing an intake air to an internal combustion engine used in a vehicle travelling, and measures at least a flowing amount of the intake air suctioned in the internal combustion engine. In this case, the intake air may be an air used for a combustion, and the measurement device measures a flowing amount of the air. The intake duct 1 may be an outlet of an air cleaner or an intake pipe.

An attachment hole penetrating a wall of the intake duct 1 to communicate with an interior and an exterior of the intake duct 1 is arranged at a position of the intake duct 1 where the measurement device is installed. The measurement device includes a cover portion 2 blocking the attachment hole.

The measurement device includes a bypass housing 3 that is seamlessly bonded to the cover portion 2, and a flowing amount sensor 4 provided in the bypass housing 3.

Since the attachment hole is provided in the intake duct 1, the attachment hole is blocked by the cover portion 2 after the bypass housing 3 is inserted into the intake duct 1 from an exterior of the attachment hole. The measurement device is assembled to the intake duct 1 by fastening the cover portion 2 to the intake duct 1 by using a fastening body such as a tapping screw.

The bypass housing 3 that is made of a resin material is a passage forming member that forms a passage. According to the present disclosure, a configuration of the passage formed in the bypass housing 3 is not limited. For example, according to the present embodiment, the bypass housing 3 includes a main air passage that is in the intake duct 1, and a first sub air passage that is a bypass passage 5 and a second sub air passage that is a sub bypass passage 6 through which a part of the intake air flowing through the main air passage flows.

The bypass passage 5 is an air passage through which a part of the intake air flowing through an interior of the intake duct 1, and is a passage along a flowing direction of the intake air in the intake duct 1. The bypass passage 5 includes an air inlet 5a placed at an upstream end of the bypass passage 5 and an air outlet 5b placed at a downstream end of the bypass passage 5. The air outlet 5b includes an outlet throttle that throttles a flow of the intake air passing through the bypass passage 5.

The sub bypass passage 6 includes an inlet 6a into which a part of the flow of the intake air throttled by the outlet throttle flows, and an outlet 6b returning the flow of the intake air passing through the sub bypass passage 6 to the intake duct 1. The sub bypass passage 6 is a bypass passage that rotates the intake air flowing from the inlet 6a in the bypass housing 3 and returns the intake air to the intake duct 1.

Figure 1B:
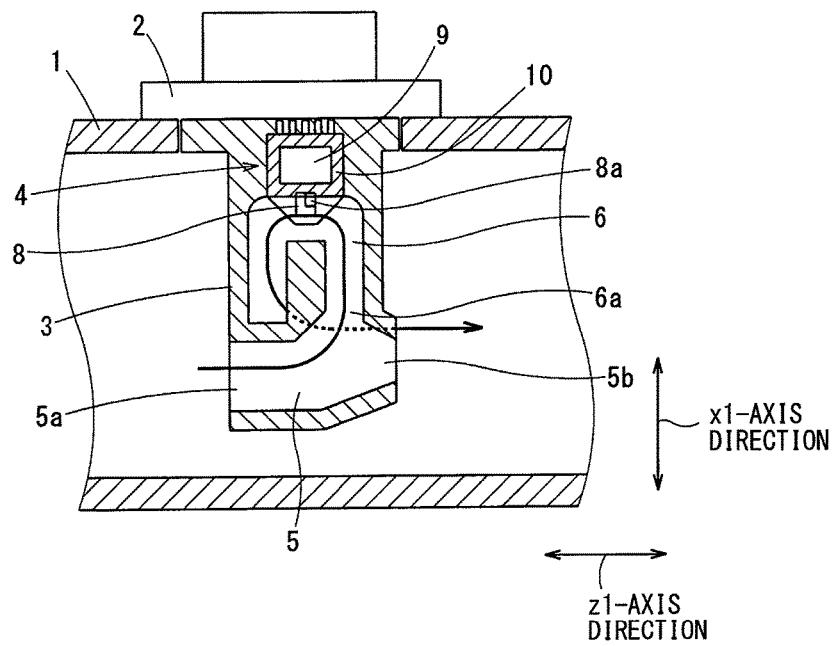
FIG. 1B is a cross section of the measurement device taken in the flowing direction of the intake air, according to the first embodiment.

As shown in FIGS. 1A and 1B, the outlet 6b of the sub bypass passage 6 is arranged at a position out of the bypass passage 5. However, according to the present disclosure, it is not limited to FIGS. 1A and 1B. For example, the outlet 6b of the sub bypass passage 6 may be opened to an interior of the bypass passage 5 so as to return the intake air passing through the sub bypass passage 6 to the bypass passage 5.

A connector 7 connected with an engine control unit (ECU) is provided on the cover portion 2. The cover portion 2 and the bypass housing 3 are made of a resin material that is common.

The flowing amount sensor 4 is a thermal sensor that is well-known, and measures a flowing amount of the intake air passing through the sub bypass passage 6 based on a thermal detection value. According to the present disclosure, the flowing amount sensor 4 is not limited. For example, the flowing amount sensor 4 may be a chip such as a thin-film substrate or a bobbin-type resistor such as a single-type resistor.

As shown in FIG. 1B, the flowing amount sensor 4 is a chip that is assembled and is arranged in the bypass housing 3. The flowing amount sensor 4 includes a sensor substrate 8 where a flowing amount detection portion 8a measuring the flowing amount of the intake air is provided, a flowing amount sensor circuit 9 that is electrically connected with the connector 7, and a circuit housing 10 that receives the flowing amount sensor circuit 9.

The flowing amount sensor circuit 9 corrects the flowing amount detected by the flowing amount detection portion 8a based on an intake temperature which is a temperature of the intake air that is not heated by a heater, converts a flowing amount signal after being corrected to a digital signal, and outputs the digital signal. In this case, the digital signal may be obtained by a frequency modulation.

According to the present embodiment, the measurement device includes an intake temperature sensor 11 measuring the temperature of the intake air passing through the interior of the intake duct 1. In this case, the temperature of the intake air passing through the interior of the intake duct 1 is the temperature of the intake air suctioned into the internal combustion engine.

As shown in FIG. 1A, the intake temperature sensor 11 is placed at a position out of the bypass housing 3, and measures the temperature of the intake air passing through an exterior of the bypass housing 3. Specifically, the intake temperature sensor 11 is placed at a position separated from the bypass housing 3 by a predetermined distance, so as not to be affected by a heat transmission of the bypass housing 3.

As shown in FIG. 1A, the intake temperature sensor 11 is a thermistor element, and includes a thermistor body having a resistance value varying depending on a temperature and two lead wires extending from the thermistor body. The lead wires are supported by the cover portion 2 or the bypass housing 3, and then the thermistor body is supported at a position separated from the bypass housing 3 by a predetermined distance. In this case, the intake temperature sensor 11 is placed at a position substantially being not in contact with other components except the lead wires.

According to the present disclosure, an intake temperature signal that is a signal corresponding to the intake temperature measured by the intake temperature sensor 11 may be a voltage obtained from a variation of the resistance value. Alternatively, similar to the flowing amount of the intake air, the intake temperature signal may be outputted after being converted to a digital signal. In this case, the digital signal may be obtained by a frequency modulation.

Referring to FIGS. 1A, 1B, 2A, 2B, and 2C, the humidity sensor 12 will be described.

Hereafter, as shown in FIG. 1A, an x1-axis direction indicates a direction of the intake duct 1, and an y1-axis direction indicates a direction perpendicular to the x1-axis direction. As shown in FIG. 1B, a z1-axis direction indicates the flowing direction of the intake air flowing through the exterior of the bypass housing 3.

Figure 2A:
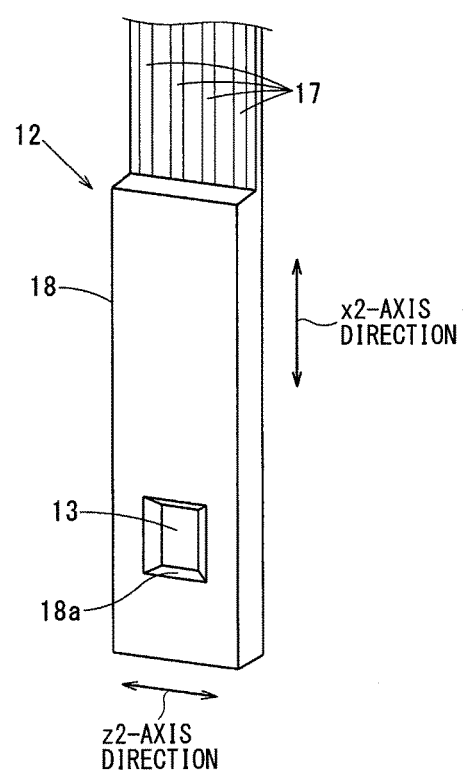
FIG. 2A is a diagram showing an outline of a humidity sensor, according to the first embodiment.
Figure 2B:
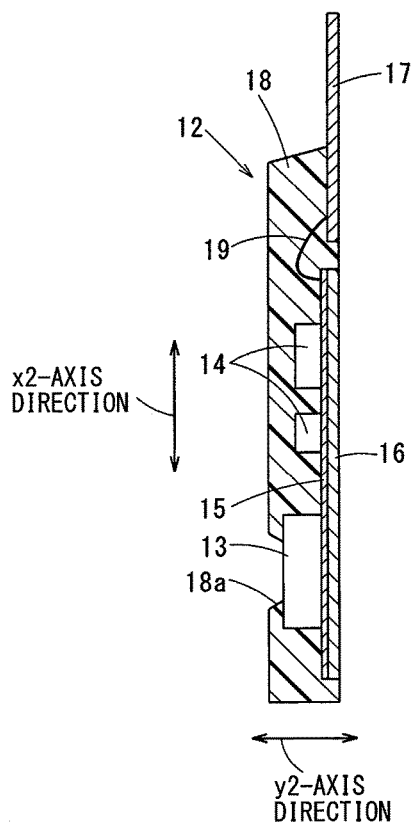
FIG. 2B is a cross section of the humidity sensor taken in a longitudinal direction of the humidity sensor, according to the first embodiment.
Figure 2C:
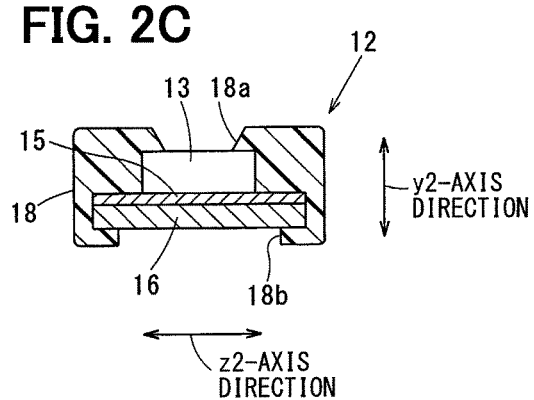
FIG. 2C is a cross section of the humidity sensor taken in a direction perpendicular to the longitudinal direction, according to the first embodiment.

According to the present embodiment, the humidity sensor 12 is a plate shape and has a cross section that is a substantially rectangle shape. According to the present disclosure, a shape of the humidity sensor 12 is not limited. Hereafter, as shown in FIG. 2B, an x2-axis direction indicates a direction parallel to a longest edge of the humidity sensor 12, and a y2-axis direction indicates a direction parallel to a shortest edge of the humidity sensor 12. As shown in FIG. 2C, a z2-axis direction indicates a direction parallel to an edge of the humidity sensor 12 that is shorter than the longest edge and is longer than the shortest edge.

The measurement device includes the humidity sensor 12 measuring a humidity of the intake air passing through the interior of the intake duct 1. In this case, the humidity of the intake air passing through the interior of the intake duct 1 is a humidity of the intake air suctioned into the internal combustion engine.

As shown in FIG. 1A, the humidity sensor 12 is placed at a position out of the bypass housing 3, that is, the humidity sensor 12 is placed at a position in the vicinity of the bypass housing 3. The humidity sensor 12 measures the humidity of the intake air passing through the exterior of the bypass housing 3, that is, the humidity sensor 12 measures the humidity of the intake air passing through a position in the vicinity of the bypass housing 3.

Specifically, the humidity sensor 12 is placed at a position separated from the bypass housing 3 by a predetermined distance, so as not to be affected by the heat transmission of the bypass housing 3. In this case, the heat transmission of the bypass housing 3 is a heat transmitted to the bypass housing 3 through the cover portion 2.

According to the present embodiment, the humidity sensor 12 is placed at position where the x2-axis direction is parallel to the x1-axis direction, the y2-axis direction is parallel to the y1-axis direction, and the z2-axis direction is parallel to the z1-axis direction. In other words, a surface of the humidity sensor 12 that is a front surface or a rear surface where an area is large is placed at a position to be parallel to the flowing direction of the intake air.

The humidity sensor 12 includes a humidity detection element 13 that measures the humidity of the intake air passing through the exterior of the bypass housing 3, a humidity sensor circuit 14 that outputs a humidity signal of the humidity detection element 13 to external, a circuit substrate 15 that is thin and is provided with the humidity detection element 13 and the humidity sensor circuit 14, a heat discharge plate 16 that is made of a metal and is a heat discharge portion and is directly in contact with the intake air flowing through the exterior of the bypass housing 3 and is thermally bonded to the humidity detection element 13 and the humidity sensor circuit 14 through the circuit substrate 15, plural lead pins 17 that are placed at positions such that a part of each of the lead pins 17 is exposed to the connector 7, and a mold resin 18 that molds parts of the humidity sensor 12 such as the humidity detection element 13 and the heat discharge plate 16.

Alternatively, the lead pins 17 may be placed at positions in the cover portion 2 where the lead pins 17 are connected with the flowing amount sensor circuit 9 through a terminal. According to the present embodiment, the lead pins 17 are equivalent to an electrical connection portion that is made of a metal and is placed at a position in the vicinity of a wall surface of the intake duct 1.

Further, the humidity detection element 13 and the heat discharge plate 16 are almost directly thermally bonded to each other. In other words, the circuit substrate 15 that is thin does not affect the heat transmission.

The humidity detection element 13 is an element of an electrostatic capacity type that is well known, and is not limited. For example, a humidity detection IC that is sale at a market may be used as the humidity detection element 13.

According to the present embodiment, the humidity detection IC may include a humidity detection portion that has an electrostatic capacity varies depending on a relative humidity of an air being in contact with, an amplification portion that converts a variation of the electrostatic capacity to the humidity signal that is a voltage signal, and a correction circuit that corrects the humidity signal based on an ambient temperature and then outputs the humidity signal.

Similar to the flowing amount signal and the intake temperature signal, the humidity sensor circuit 14 converts the humidity signal outputted by the humidity detection element 13 by a frequency modulation and then outputs the humidity signal to the ECU. According to the present embodiment, the humidity sensor circuit 14 includes plural electrical components such as a capacitor, and a resistor. According to the present disclosure, the humidity sensor circuit 14 is not limited.

The circuit substrate 15 is an insulator film that is made of resin and is thin and has a flexibility. The circuit substrate 15 includes an attachment surface to which the humidity detection element 13 and the humidity sensor circuit 14 are mounted, and a print wire which is conductive is only printed on the attachment surface. In this case, the print wire may be a print pattern. The print wire is electrically connected with the electrical components constituting the humidity detection element 13 and the humidity sensor circuit 14.

The circuit substrate 15 is a rectangle shape and extends in the x2-axis direction. The humidity detection element 13 is mounted to a distal portion of the circuit substrate 15 which is separated from the cover portion 2 supporting the humidity sensor 12. According to the present embodiment, the distal portion of the circuit substrate 15 is placed at a position close to a center axis of the intake duct 1. The humidity sensor circuit 14 is mounted to a position of the circuit substrate 15 between the cover portion 2 and the humidity detection element 13.

The heat discharge plate 16 is made of a metal that is excellent in heat transmission such as aluminum or copper, is a plate member has a heat discharge capability higher than that of a resin, and is thermally bonded to a rear surface of the humidity detection element 13 through the circuit substrate 15. The humidity detection element 13 includes the rear surface and a front surface, and the front is directly in contact with the intake air and is opposite to the rear surface.

The heat discharge plate 16 is a plate shape that is a rectangle shape, and has dimensions in the x2-axis direction and in the z2-axis direction which are substantially as the same as those of the circuit substrate 15. The dimension of the heat discharge plate 16 in the x2-axis direction is longer than the dimension of the heat discharge plate 16 in the z2-axis direction. The heat discharge plate 16 has a dimension of a thickness that is a dimension in the y2-axis direction is set to a value greater than or equal to 0.5 mm, so as to decrease a heat resistance of the heat discharge plate 16. According to the present disclosure, it is preferable that the dimension of the thickness is set to a value greater than or equal to 0.8 mm, and it is more preferable that the dimension of the thickness is set to a value greater than or equal to 1 mm.

The heat discharge plate 16 includes a front surface where the circuit substrate 15 is mounted to and a rear surface that is opposite to the front surface. Almost an entire of the rear surface of the heat discharge plate 16 is exposed to an exterior of the mold resin 18, and is directly in contact with the intake air flowing through the exterior of the bypass housing 3.

The heat discharge plate 16 also functions as a support plate supporting the circuit substrate 15. According to the present embodiment, the heat discharge plate 16 and the circuit substrate 15 is bonded to each other by a bonding agent, and then are molded by the mold resin 18. According to the present disclosure, the heat discharge plate 16 and the circuit substrate 15 are not limited to be bonded to each other by a bonding agent.

Each of the lead pins 17 is an elongated metal plate obtained from a metal plate having conductive by using a press processing. According to the present disclosure, the lead pin 17 is not limited, and may be obtained by other methods or operations. Each of the lead pins 17 is electrically connected with the print wire of the circuit substrate 15 through a wire bonding 19.

After the lead pin 17 is electrically connected with the print wire of the circuit substrate 15, the lead pin 17 is molded by the mold resin 18 in a case where a part of the lead pin 17 is exposed to an exterior of the mold resin 18.

According to the present embodiment, the part of the lead pin 17 exposed to the exterior of the mold resin 18 is placed at a position in the connector 7 that is integrally bonded to the cover portion 2. Alternatively, the part of the lead pin 17 is connected with the flowing amount sensor circuit 9 in the cover portion 2.

The mold resin 18 is a resin having an insulation and molds components constituting the humidity sensor 12. The mold resin 18 protects the components constituting the humidity sensor 12, and ensures a rigidity of the humidity sensor 12.

The mold resin 18 includes a window portion 18a that directly introduces the intake air to a part of the humidity detection element 13. The part of the humidity detection element 13 is the humidity detection portion.

The mold resin 18 includes a heat discharge port 18b through which almost an entire of the rear surface of the heat discharge plate 16 is exposed to the intake air.

An end of the mold resin 18 in a longitudinal direction of the mold resin 18 is molded by a resin material forming the cover portion 2. Since the mold resin 18 is molded to the cover portion 2, the measurement device is supported by the humidity sensor 12.

As shown in FIG. 1A, the front surface of the humidity detection element 13 is placed at a position facing the bypass housing 3, and the rear surface of the heat discharge plate 16 is placed at a position facing in a direction opposite to a direction toward the bypass housing 3. However, according to the present disclosure, a position arrangement of the humidity detection element 13 and the heat discharge plate 16 is not limited. For example, the rear surface of the heat discharge plate 16 may be placed at a position facing the bypass housing 3, and the front surface of the humidity detection element 13 may be placed at a position facing in a direction opposite to the direction toward the bypass housing 3.

As shown in FIG. 2C, the mold resin 18 has a cross section that is a substantially rectangle shape. However, according to the present disclosure, a shape of the mold resin 18 is not limited. The mold resin 18 may include an upstream end and a downstream which are streamline shapes, or may include the upstream end and the downstream which are sharp shapes.

The humidity sensor 12 mounted to the measurement device forcibly executes a heat exchange between the humidity detection element 13 and the intake air flowing through the exterior of the bypass housing 3 via the heat discharge plate 16.

Therefore, when the intake duct 1 and the cover portion 2 receive heat from an engine room, a temperature of the humidity detection element 13 can approach to be substantially equal to the temperature of the intake air flowing through the exterior of the bypass housing 3. In this case, the temperature of the intake air flowing through the exterior of the bypass housing 3, which is the temperature of the intake air that is separated from the intake duct 1, is the temperature of the intake air which is not affected by a heat of the engine room. Thus, when the engine room is in a high temperature environment, a deterioration of an accuracy of a detection of an intake humidity can be prevented, and the intake humidity that is a humidity of the intake air can be accurately measured by the humidity sensor 12.

According to the present embodiment, the humidity sensor 12 extends in the x2-axis direction. Further, the heat discharge plate 16 extends in the x2-axis direction so as to be directly in contact with the intake air.

Thus, the heat transmitted from the cover portion 2 to the humidity sensor 12 is surely discharged to a space between the cover portion 2 and the humidity detection element 13 before being transmitted to the humidity detection element 13.

Therefore, the temperature of the humidity detection element 13 can approach to be substantially equal to the temperature of the intake air flowing through the exterior of the bypass housing 3, and the accuracy of the detection of the humidity in the humidity sensor 12 can be further improved.

Further, since the heat discharge portion is provided, a flexibility of a configuration of the measurement device including the humidity detection element can be improved.

According to the present embodiment, when a heat is generated due to an operation of the humidity sensor circuit 14, the humidity sensor 12 can discharge the heat through the heat discharge plate 16. Therefore, a malfunction that the temperature of the humidity detection element 13 is increased due to the heat generated by the humidity sensor circuit 14 can be prevented, and the deterioration of the accuracy of the detection of the humidity sensor 12 generated due to the heat generated by the humidity sensor circuit 14 can be prevented.

[Second Embodiment]

Figure 3:
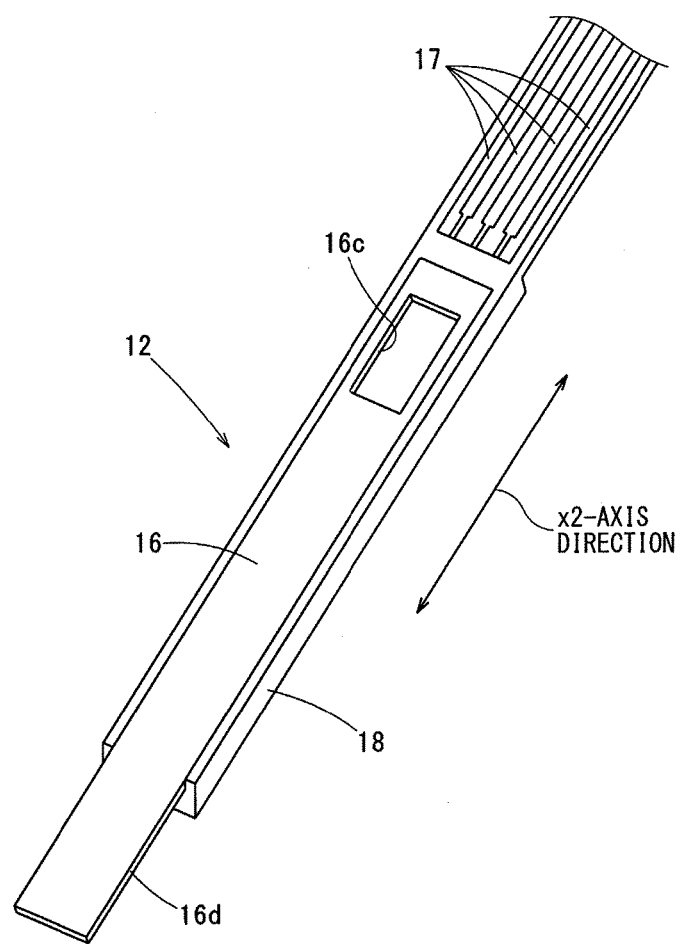
FIG. 3 is a diagram showing a rear of the humidity sensor, according to a second embodiment and a third embodiment of the present disclosure.

Referring to FIG. 3, a second embodiment of the present disclosure will be described. In the following embodiments, the substantially same parts or components as those in the first embodiment may be indicated with the same reference numerals.

According to the second embodiment, the heat discharge plate 16 includes a protrusion portion 16d that extends to the exterior of the mold resin 18 so as to enlarge a surface where the heat discharge plate 16 is in contact with the intake air.

According to the present disclosure, a shape of the protrusion portion 16d is not limited. For, example, according to the second embodiment, a dimension of the protrusion portion 16d in the x2-axis direction is longer than a dimension of the mold resin 18 in the x2-axis direction, and a distal of the heat discharge plate 16 extends toward the center axis of the intake duct 1.

Since the protrusion portion 16d is provided, a heat discharge capability of the heat discharge plate 16 can be improved.

According to the second embodiment, since the protrusion portion 16d is placed at a position close to the center axis of the intake duct 1, a heat of a part of the intake air which is most hardly affected by the engine room can be transmitted to the humidity detection element 13.

Thus, since the temperature of the humidity detection element 13 can approach to the temperature of the intake air which is most hardly affected by the engine room, the accuracy of the detection of the humidity in the humidity sensor 12 can be further improved.

[Third Embodiment]

Referring to FIG. 3, a third embodiment of the present disclosure will be described.

According to the third embodiment, the heat discharge plate 16 includes a hollow portion 16c that prevents a heat transmission in the heat discharge plate 16 in the x2-axis direction at a position of the heat discharge plate 16 between the cover portion 2 and a position that the heat discharge plate 16 is thermally bonded to the humidity detection element 13. In this case, the position of the heat discharge plate 16 where the hollow portion 16c is placed is placed between a position in the vicinity of the wall surface of the intake duct 1 and a position that the heat discharge plate 16 is thermally bonded to the humidity detection element 13. The hollow portion 16c may be a notch portion or an opening portion.

Thus, when the cover portion receives heat from the engine room and the heat of the cover portion 2 is transmitted to a base end of the heat discharge plate 16, since the heat transmission is blocked by the hollow portion 16c, the heat of the cover portion 2 is prevented from being transmitted to the humidity detection element 13 through the heat discharge plate 16. The base end of the heat discharge plate 16 is a part of the heat discharge plate 16 where the circuit substrate 15 on which the wire bonding 19 is located is supported. Thus, the temperature of the humidity detection element 13 can surely approach the temperature of the intake air, and the accuracy of the detection of the humidity in the humidity sensor 12 can be further improved.

[Fourth Embodiment]

Figure 4:
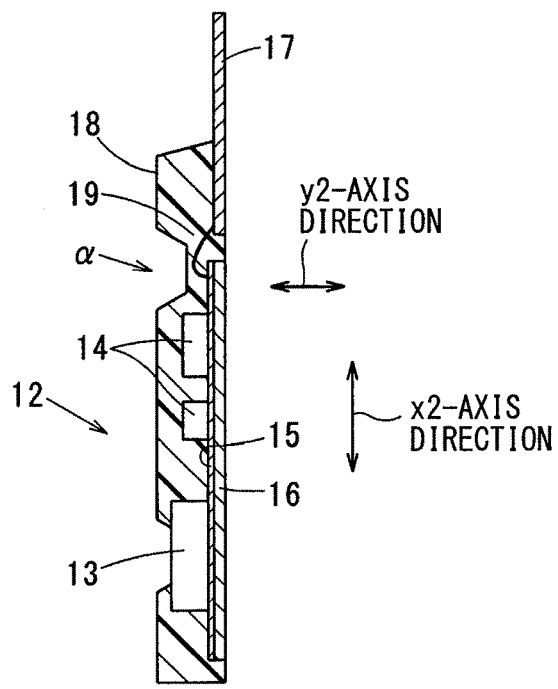
FIG. 4 is a cross section of the humidity sensor taken in the longitudinal direction, according to a fourth embodiment of the present disclosure.

Referring to FIG. 4, a fourth embodiment of the present disclosure will be described.

According to the fourth embodiment, the humidity sensor 12 includes a contraction portion α that is placed at a position of the mold resin 18 closer to the wall surface of the intake duct 1 than the humidity detection element 13 is. A dimension of a thickness of the contraction portion α that is a dimension in the y2-axis direction is thinner than a dimension of a thickness of other parts of the mold resin 18.

According to the fourth embodiment, the humidity sensor 12 includes the contraction portion α that has a temperature resistance larger than other parts of the mold resin 18.

When the cover portion 2 receives heat from the engine room, the contraction portion α can suppress the heat transmission from the cover portion 2 to the humidity detection element 13. According to the present embodiment, the contraction portion α is a position where the temperature resistance is large. Thus, the temperature of the humidity detection element 13 can surely approach the temperature of the intake air, and the accuracy of the detection of the humidity in the humidity sensor 12 can be further improved.

[Fifth Embodiment]

Figure 5:
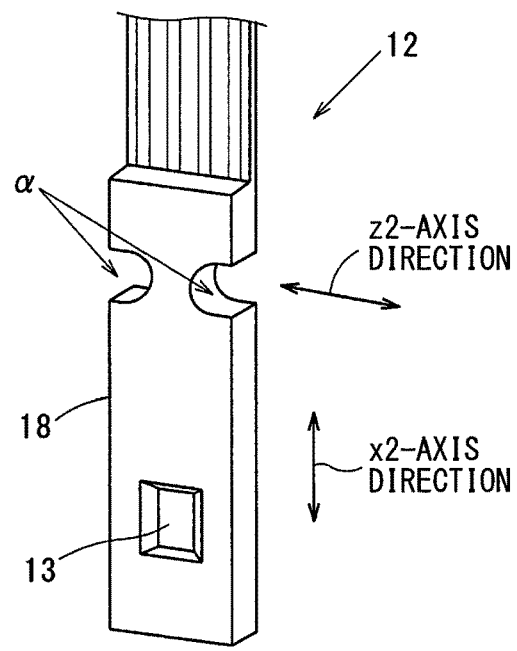
FIG. 5 is a diagram showing a front of the humidity sensor, according to a fifth embodiment of the present disclosure.

Referring to FIG. 5, a fifth embodiment of the present disclosure will be described.

According to the fifth embodiment, the humidity sensor 12 includes a contraction portion α that is placed at a position closer to the wall surface of the intake duct 1 than the humidity detection element 13 is. A dimension of a width of the contraction portion α that is a dimension in the z2-axis direction is smaller than a dimension of a width of other parts of the mold resin 18.

According to the fifth embodiment, similar to the fourth embodiment, the humidity sensor 12 includes the contraction portion α that has a temperature resistance larger than other parts of the mold resin 18.

Thus, the same effects as the fourth embodiment can be obtained.

[Sixth Embodiment]

Figure 6:
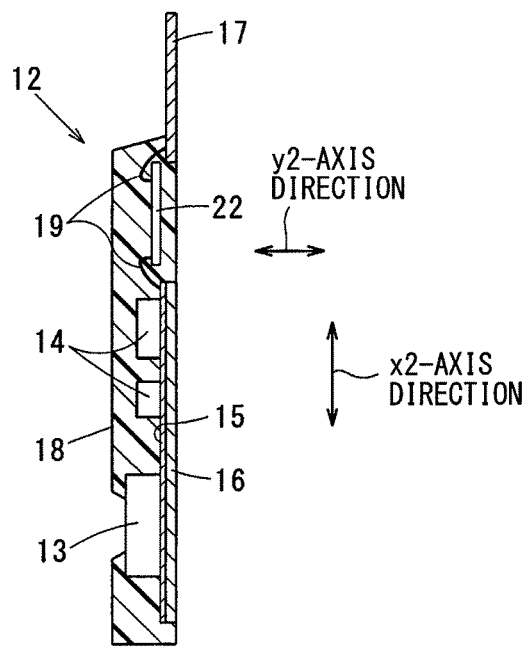
FIG. 6 is a cross section of the humidity sensor taken in the longitudinal direction, according to a sixth embodiment of the present disclosure.

Referring to FIG. 6, a sixth embodiment of the present disclosure will be described.

According to sixth embodiment, the humidity sensor 12 includes a heat resistor 22 that is placed at a position between the circuit substrate 15, the heat discharge plate 16, and the lead pins 17. The heat resistor 22 blocks the heat transmission.

The heat resistor 22 is an insulator member having a heat transmission rate smaller than that of a metal forming the lead pins 17 or the heat discharge plate 16, such as a ceramic.

A signal wire that is conductive is arranged on a surface of the heat resistor 22 by a printing technology. The lead pins 17 and the print wire of the circuit substrate 15 are electrically connected with each other through the signal wire arranged on the surface of the heat resistor 22.

Specifically, the lead pins 17 are electrically connected with the signal wire of the heat resistor 22 through the wire bonding 19, and the signal wire on the heat resistor 22 is electrically connected with the print wire of the circuit substrate 15 through the wire bonding 19.

When the cover portion 2 receives heat from the engine room, a malfunction that the heat is transmitted from the lead pins 17 supported by the cover portion 2 to the heat discharge plate 16 can be suppressed by the heat resistor 22. Therefore, since the temperature of the humidity detection element 13 can surely approach the temperature of the intake air, the accuracy of the detection of the humidity in the humidity sensor 12 can be further improved.

[Seventh Embodiment]

Figure 7:
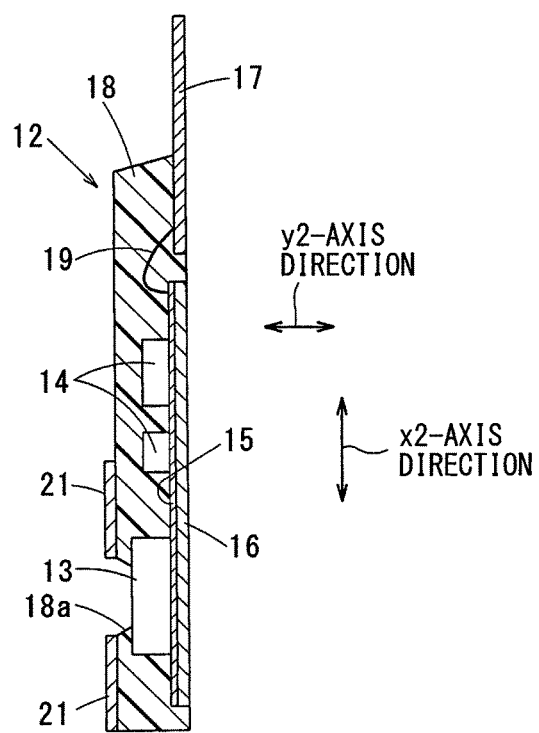
FIG. 7 is a cross section of the humidity sensor taken in the longitudinal direction, according to a seventh embodiment of the present disclosure.

Referring to FIG. 7, a seventh embodiment of the present disclosure will be described.

According to the seventh embodiment, a metal plate 21 that is excellent in heat transmission is arranged to cover at least a part of a periphery of the window portion 18a in the mold resin 18. The metal plate 21 may be made of an aluminum or a copper.

The metal plate 21 may be a ring plate shape that covers an entire periphery of the window portion 18a. Alternatively, the metal plate 21 may have at least one part. In other words, plural metal plates 21 may be arranged to cover at least a part of the periphery of the window portion 18a.

Further, it is not limited that the metal plate 21 is bonded to the mold resin 18 by only one processing. For example, a part of the metal plate 21 may be molded by the mold resin 18. Alternatively, the metal plate 21 may be fixed on a surface of the mold resin 18 by a bonding agent.

Since the temperature of the humidity detection element 13 can approach the temperature of the intake air in a case where the heat discharge plate 16 and the metal plate 21 are arranged on the rear surface and the front surface of the humidity detection element 13, respectively, the accuracy of the detection of the humidity in the humidity sensor 12 can be further improved.

[Eighth Embodiment]

Figure 8:
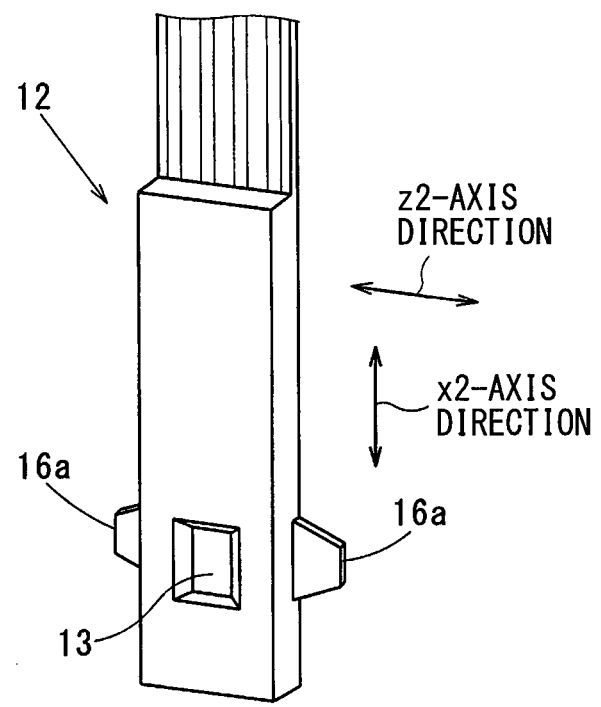
FIG. 8 is a diagram showing the front of the humidity sensor, according to an eighth embodiment of the present disclosure.

Referring to FIG. 8, an eighth embodiment of the present disclosure will be described.

According to the eighth embodiment, the heat discharge plate 16 includes a width extension portion 16a that has a width larger than a width of other parts of the heat discharge plate 16. The width extension portion 16a is placed at a position where the heat discharge plate 16 is thermally bonded to the humidity detection element 13. The width of the width extension portion 16a is width along the flowing direction of the intake air, that is, the width of the width extension portion 16a is a dimension in the z2-axis direction.

Since the heat discharge capability of the heat discharge plate 16 can be improved by the width extension portion 16a at the position where the heat discharge plate 16 is thermally bonded to the humidity detection element 13, the temperature of the humidity detection element 13 can surely approach the temperature of the intake air. Therefore, the accuracy of the detection of the humidity in the humidity sensor 12 can be further improved.

[Ninth Embodiment]

Referring to FIGS. 9A and 9B, a ninth embodiment of the present disclosure will be described.

According to the ninth embodiment, the heat discharge plate 16 includes a heat discharge fin 16b that is placed at a position to be directly in contact with the intake air so as to enlarge a surface where the heat discharge plate 16 is in contact with the intake air.

Specifically, plural heat discharge fins 16b which are rib shapes are arranged on the rear surface of the heat discharge plate 16, and the heat discharge capability of the heat discharge plate 16 is improved by the heat discharge fins 16b.

As shown in FIG. 9A, the heat discharge fins 16b are arranged to be parallel to the z2-axis direction that is also parallel to the flowing direction of the intake air.

As shown in FIG. 9B, the heat discharge fins 16b are arranged to be parallel to the x2-axis direction that is perpendicular to the flowing direction of the intake air.

Since the heat discharge capability of the heat discharge plate 16 is improved by the heat discharge fins 16b, the temperature of the humidity detection element 13 can surely approach the temperature of the intake air. Therefore, the accuracy of the detection of the humidity in the humidity sensor 12 can be further improved.

[Tenth Embodiment]

Figure 10:
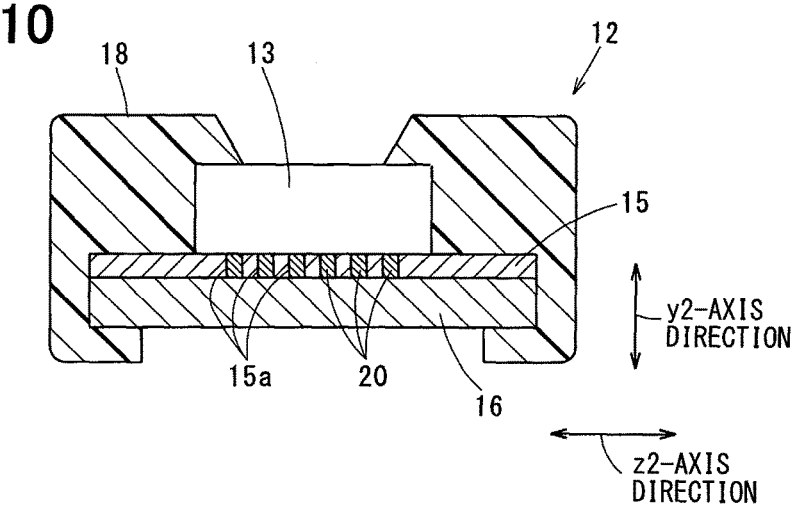
FIG. 10 is a cross section of the humidity sensor taken in a direction perpendicular to the longitudinal direction, according to a tenth embodiment of the present disclosure.

Referring to FIG. 10, a tenth embodiment of the present disclosure will be described.

According to the tenth embodiment, the circuit substrate 15 includes plural via holes 15a which are placed at a position of the circuit substrate 15 where the humidity detection element 13 is mounted to. The via holes 15a penetrate a front surface and a rear surface of the circuit substrate 15. The via holes 15a are filled with a metal 20 that is excellent in heat transmission. The metal 20 may be an aluminum or a copper.

Thus, a heat resistance between the humidity detection element 13 and the heat discharge plate 16 can be decreased. In other words, a heat bonding of the humidity detection element 13 and the heat discharge plate 16 can be improved. Thus, the temperature of the humidity detection element 13 can surely approach the temperature of the intake air, and the accuracy of the detection of the humidity in the humidity sensor 12 can be further improved.

[Eleventh Embodiment]

Figure 11A:
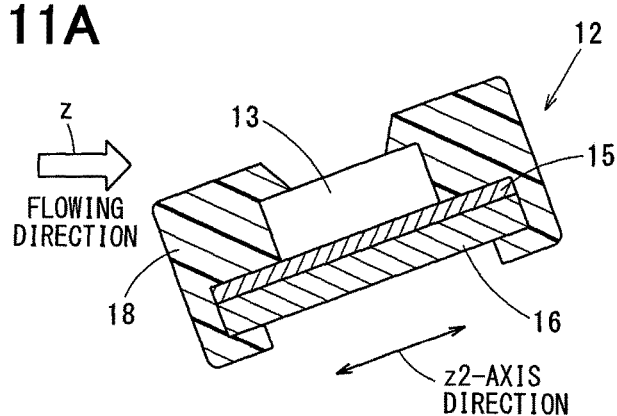
FIGS. 11A and 11B are cross sections of the humidity sensor taken in a direction perpendicular to the longitudinal direction, according to an eleventh embodiment of the present disclosure.
Figure 11B:
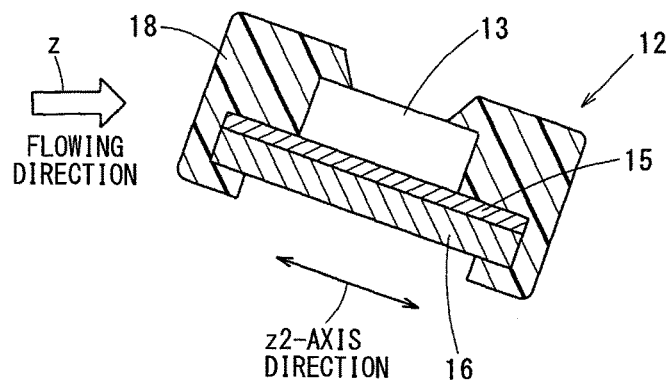
Figure 12A:
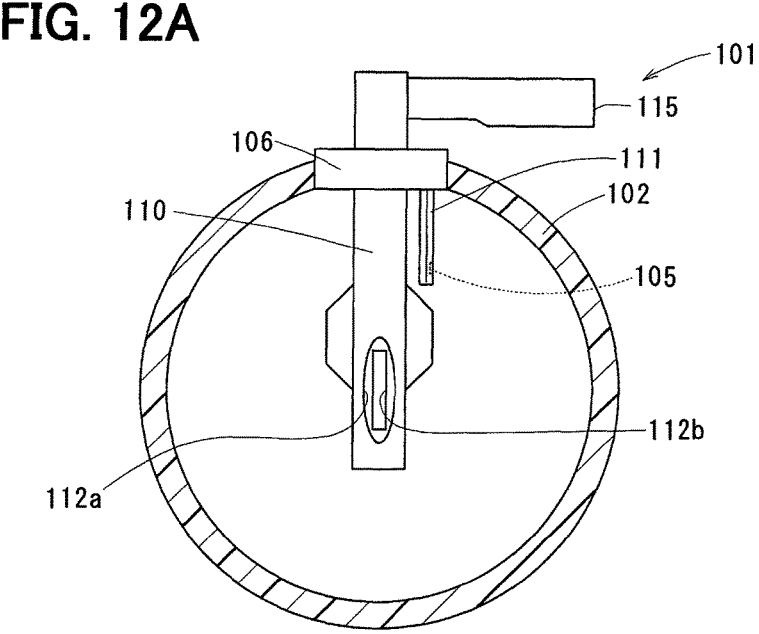
FIG. 12A is a diagram showing an outline of the measurement device viewed from the upstream in the flowing direction of the intake air, according to a twelfth embodiment of the present disclosure.
Figure 12B:
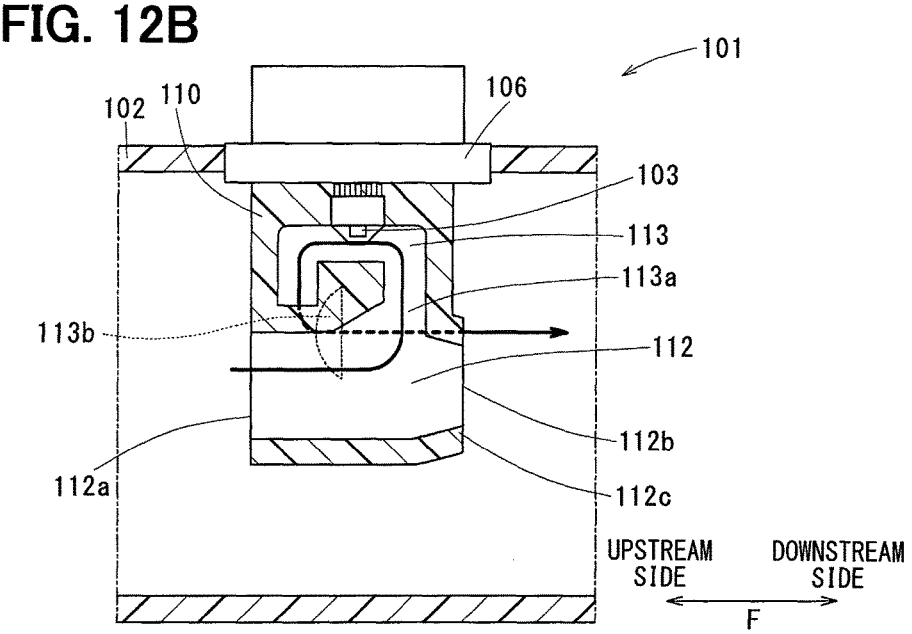
FIG. 12B is a cross section of the measurement device taken in the flowing direction of the intake air, according to the twelfth embodiment.

Referring to FIGS. 11A and 11B, an eleventh embodiment of the present disclosure will be described.

According to the eleventh embodiment, the z2-axis direction of the humidity sensor 12 is tilted relative to the flowing direction of the intake air in the intake duct 1.

In other words, the heat discharge plate 16 is tilted relative to the flowing direction of the intake air passing through the interior of the intake duct 1.

As shown in FIG. 11A, a downstream end of the front surface of the humidity sensor 12 is placed to approach the bypass housing 3.

As shown in FIG. 11B, an upstream end of the front surface of the humidity sensor 12 is placed to approach the bypass housing 3.

Since the heat discharge plate 16 is tilted relative to the flowing direction of the intake air, the intake air more strongly collides with the heat discharge plate 16, and the heat discharge capability of the heat discharge plate 16 can be improved. Thus, since the temperature of the humidity detection element 13 can surely approach the temperature of the intake air, the accuracy of the detection of the humidity in the humidity sensor 12 can be further improved.

[Twelfth Embodiment]

Referring to FIGS. 12A, 12B, 13A, 13B, and 13C, a measurement device 101 according to a twelfth embodiment of the present disclosure will be described.

The measurement device 101 is mounted to an intake duct 102 through which the intake air suctioned to the internal combustion engine in the vehicle travelling. The measurement device 101 includes a flowing amount sensor 103 and a humidity sensor 105 which are arranged in the intake duct 102. The measurement device 101 measure a flowing amount and a humidity of the intake air flowing through the intake duct 102.

Hereafter, the flowing direction of the intake air in the intake duct 102 is an F direction.

An attachment hole penetrating a wall of the intake duct 102 to communicate with an interior and an exterior of the intake duct 102 is arranged at a position of the intake duct 102 where the measurement device 101 is installed. The measurement device 101 includes a cover portion 106 blocking the attachment hole.

The measurement device 101 includes a first protrusion 110 and a second protrusion 111 which protrude from the cover portion 106.

In this case, the first protrusion 110 and the second protrusion 111 are seamlessly bonded to the cover portion 106, and protrude from the cover portion 106 in the same direction.

The first protrusion 110 supports the flowing amount sensor 103 and protrudes toward an inner periphery of the intake duct 102.

The first protrusion 110 is made of a resin material, and forms a passage.

A configuration of the passage formed in the first protrusion 110 is that the passage includes a main bypass passage 112 and a sub bypass passage 113.

The main bypass passage 112 is a passage through which a part of the intake air flowing through the intake duct 102 flows, and the main bypass passage 112 is a passage parallel to the flowing direction of the intake air in the intake duct 102. The main bypass passage 112 includes an air inlet 112a placed at an upstream end of the main bypass passage 112, and an air outlet 112b placed at a downstream end of the main bypass passage 112.

The air outlet 112b includes an outlet throttle 112c that throttles the flow of the intake air passing through the main bypass passage 112.

The sub bypass passage 113 includes an inlet 113a into which a part of the intake air throttled by the outlet throttle 112c flows, and an outlet 113b returning the intake air passing through the sub bypass passage 113 to the intake duct 102. The sub bypass passage 113 rotates the intake air flowing from the inlet 113a in the first protrusion 110 and introduces the intake air to the outlet 113b.

The flowing amount sensor 103 that is a chip measures the flowing amount by the heat transmission of the intake air passing through an interior of the sub bypass housing 113. The flowing amount sensor 103 has a well-known configuration that a heat resistor and a temperature measurement resistor are arranged on a surface of the flowing amount sensor 103. The flowing amount sensor 103 outputs a signal corresponding to the flowing amount of the intake air to the ECU (not shown) through a connection pin in a connector 115.

The connector 115 is integrally bonded to the cover portion 106.

The second protrusion 111 that is a rod shape protruding toward the inner periphery of the intake duct 102 to be separated from the first protrusion 110, and supports the humidity sensor 105. A protrusion direction of the second protrusion 111 that is a longitudinal direction of the second protrusion 111 is perpendicular to the F direction.

The humidity sensor 105 is laid in a surface of the second protrusion 111 and is supported by the second protrusion 111 so as to be exposed to the intake duct 102.

Specifically, the humidity sensor 105 is arranged on a side surface of the second protrusion 111 that facing a wall surface of the intake duct 102. Further, the humidity sensor 105 is laid in the second protrusion 111 such that a surface of the humidity sensor 105 is parallel to the longitudinal direction and the F direction.

The humidity sensor 105 that is an electrostatic capacity type has an electrostatic capacity varying depending on the humidity. The humidity sensor 105 has a well-known configuration that a polymer membrane having an electrostatic capacity varying depending on the humidity is arranged on the surface of the humidity sensor 105. The humidity sensor 105 outputs a signal corresponding to the humidity of the intake air to the ECU through the connection pin of the connector 115.

The second protrusion 111 includes the humidity sensor 105 that is supported by a support substrate 117 and a lead pin that is electrically connected with the humidity sensor 105. In this case, the humidity sensor 105 and the lead pin are laid in a resin material. An end of the lead pin that is the connection pin is exposed to an interior of the connector 115.

The support substrate 117 is a silicon substrate. Since the humidity sensor 105 having a strength weaker than that of the support substrate 117 is fixed to the support substrate 117, a treatment of the humidity sensor 105 is facilitated.

A vertical cross section is a cross section of the second protrusion 111 which is perpendicular to the longitudinal direction.

A parallel cross section is a cross section of the second protrusion 111 which is parallel to the longitudinal direction and the F direction.

Figure 13A:
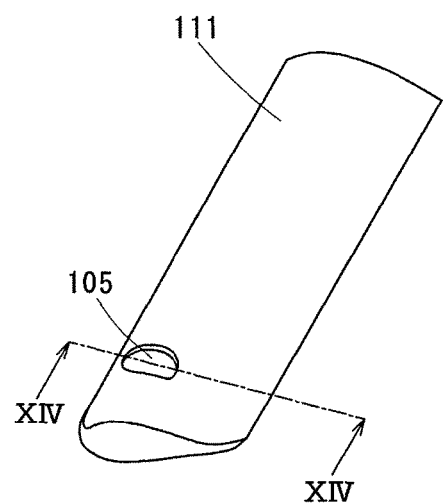
FIG. 13A is a perspective view showing a second protrusion, according to the twelfth embodiment.
Figure 13B:
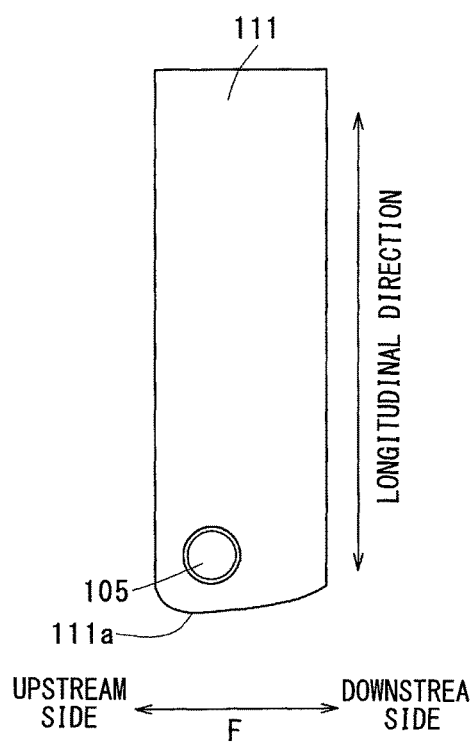
FIG. 13B is a side view showing the second protrusion viewed in a direction perpendicular to the longitudinal direction and the flowing direction of the intake air, according to the twelfth embodiment.

The second protrusion 111 is a rod shape. The humidity sensor 105 is laid in the surface of the second protrusion 111 at a distal portion in the longitudinal direction. As shown in FIGS. 13A and 13B, a shape of the vertical cross section of the second protrusion 111 is substantially the same in the longitudinal direction.

Figure 14:
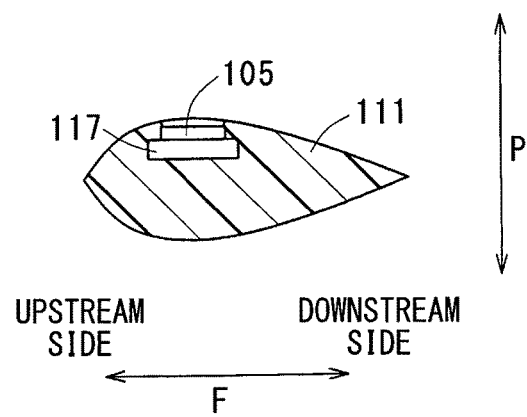
FIG. 14 is a cross section of the second protrusion taken along a line XIV-XIV in FIG. 13A, according to the twelfth embodiment.

As shown in FIG. 14, a periphery of the vertical cross section of the second protrusion 111 is a streamline shape relative to the flow of the intake air.

Specifically, a width of the vertical cross section in a P direction that is perpendicular to the F direction gradually increases and then gradually decreases from an upstream end to a downstream end in the vertical cross section.

As shown in FIG. 14, the humidity sensor 105 is placed at a position in the vertical cross section where the width of the vertical cross section in the P direction is maximum.

Figure 13C:
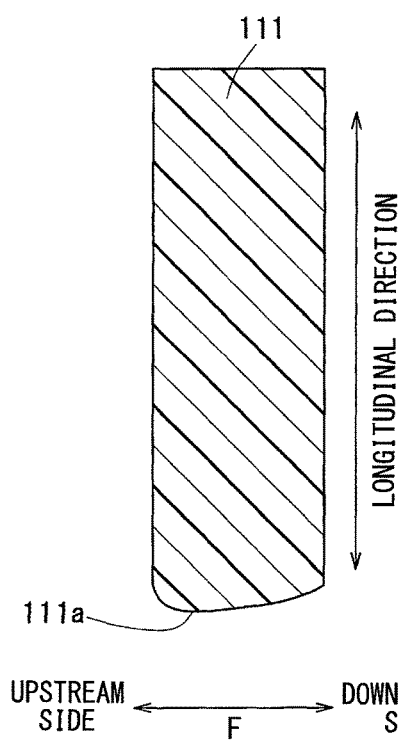
FIG. 13C is a cross section of the second protrusion taken in a direction parallel to the longitudinal direction and the flowing direction of the intake air, according to the twelfth embodiment.

As shown in FIG. 13C, the second protrusion 111 includes a protrusion end 111a, and the parallel cross section of the protrusion end 111a is a streamline shape relative to the flow of the intake air. The protrusion end 111a is the distal portion of the second protrusion 111 in the longitudinal direction.

According to the present embodiment, in the measurement device 101, the periphery of the vertical cross section of the second protrusion 111 is a streamline shape relative to the flow of the intake air.

Therefore, when the second protrusion 111 is attached to the intake duct 102, a vortex of the intake air generated on the surface of the second protrusion 111 can be suppressed.

Thus, in the measurement device 101 arranged in the intake duct 102, a pressure loss generated due to the second protrusion 111 can be suppressed.

According to the present embodiment, in the measurement device 101, the humidity sensor 105 is placed at a position in the vertical cross section where the width of the vertical cross section in the P direction is maximum.

Therefore, a flow rate of the intake air passing through the surface of the humidity sensor 105 can be increased.

Thus, when a temperature of the humidity sensor 105 is increased, the temperature of the humidity sensor 105 can be rapidly decreased, and the temperature of the humidity sensor 105 can approach the temperature of the intake air. Then, a bad effect to a detection value of the humidity generated in a case where the temperature of the humidity sensor 105 is different from the temperature of the intake air can be suppressed.

According to the present embodiment, in the measurement device 101, the parallel cross section of the protrusion end 111a of the second protrusion 111 is a stream line shape relative to the flow of the intake air.

Therefore, the vortex of the intake air generated on the surface of the protrusion end 111a can be suppressed, and the pressure loss relative to the intake air flowing through the surface of the protrusion end 111a can be decreased. Thus, the pressure loss generated due to the second protrusion 111 can be further suppressed.

The present disclosure is not limited to the embodiments mentioned above, and can be applied to various embodiments within the spirit and scope of the present disclosure.

Figure 15:
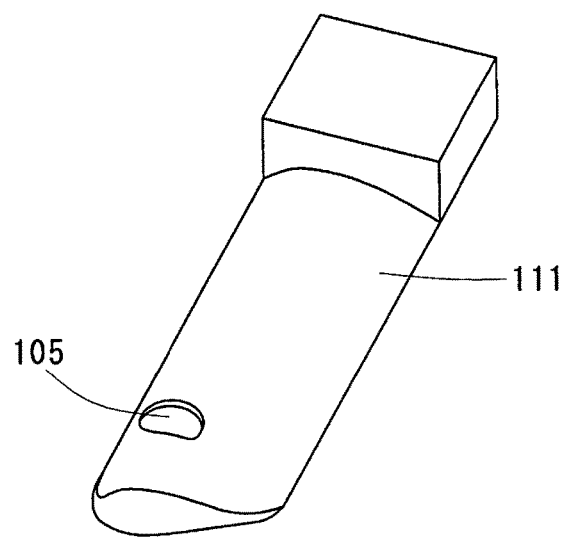
FIG. 15 is a perspective view showing the second protrusion, according to a modification example of the twelfth embodiment.

For example, according to the twelfth embodiment, the shape of the vertical cross section is substantially the same at any positions in the longitudinal direction. However, as shown in FIG. 15, an area of a part of the vertical cross section close to the cover portion 106 may be larger than that of other parts of the vertical cross section. Therefore, a strength of the second protrusion 111 can be improved.

According to the above embodiments, the heat discharge plate 16 is the heat discharge portion that is a plate shape. However, a shape or a thickness of the heat discharge portion is not limited, and various shapes may be used.

For example, the heat discharge portion may be a L shape, a J shape, a U shape, or a shape like a half part of E, such that a part of the heat discharge portion protrudes from the mold resin 18 to increase a surface where the heat discharge portion is in contact with the intake air and the heat discharge capability of the heat discharge portion is improved.

According to the above embodiments, the humidity detection element 13 is placed at a position out of the bypass housing 3. However, the humidity detection element 13 may be placed at a position in the bypass housing 3 to detect the humidity of the intake air passing through the interior of the bypass housing 3.

In this case, it is preferable that a part of the heat discharge portion protrudes to a position out of the bypass housing 3 to improve the heat discharge capability of the heat discharge portion. When a heat resistance between a region of the heat discharge portion being directly in contact with the intake air at a position out of the bypass housing 3 and a region of the heat discharge portion where the heat discharge portion is thermally bonded to the humidity detection element 13 is set to be small, the temperature of the humidity detection element 13 can approach the temperature of the intake air out of the bypass housing 3. Specifically, when a thickness of a region of the heat discharge portion where the heat discharge portion is thermally bonded to the humidity detection element 13 is increased, the temperature of the humidity detection element 13 can approach the temperature of the intake air out of the bypass housing 3.

According to the above embodiments, the humidity detection element 13 and the heat discharge portion are thermally bonded to each other through the circuit substrate 15. However, it is not limited. Specifically, the humidity detection element 13 and the heat discharge portion may be thermally bonded to each other through a mica plate that is thin. Alternatively, the humidity detection element 13 and the heat discharge portion may be directly thermally bonded to each other. Alternatively, the humidity detection element 13 and the heat discharge portion may be thermally bonded to each other by using a silicone grease so as to improve a bonding level.

While the present disclosure has been described with reference to the embodiments thereof, it is to be understood that the disclosure is not limited to the embodiments and constructions. The present disclosure is intended to cover various modification and equivalent arrangements. In addition, while the various combinations and configurations, which are preferred, other combinations and configurations,

What is claimed is:

1. A measurement device comprising:
   a housing configured to be placed at a position in an intake duct that introduces an intake air to an internal combustion engine of a vehicle, the housing defining a passage through which a part of the intake air flowing through an interior of the intake duct passes;
   a humidity detection element configured to measure a humidity of the intake air passing through a position in the vicinity of the housing;
   a heat discharge portion thermally bonded to the humidity detection element; and
   an electrical connection portion configured to be disposed between the heat discharge portion and a connector, wherein
   the heat discharge portion is separated from the electrical connection portion, and
   the humidity detection element and the heat discharge portion are integrally molded together, the heat discharge portion being exposed to the interior of the intake duct.

2. The measurement device according to claim 1, wherein
   the humidity detection element is placed at a position in the vicinity of the housing,
   the heat discharge portion is a heat discharge plate that is also a support plate supporting a circuit substrate to which the humidity detection element is mounted, and
   the heat discharge plate has a heat discharge capability higher than that of a resin.

3. The measurement device according to claim 2, wherein
   the humidity detection element and the heat discharge portion are integrally molded together with a molded resin portion that retains at least a part of the humidity detection element and the heat discharge plate.

4. The measurement device according to claim 3, wherein
   the heat discharge plate includes a protrusion portion that protrudes to an exterior of the molded resin portion and enlarges a surface where the heat discharge plate is in contact with the intake air.

5. The measurement device according to claim 2, wherein
   the heat discharge plate includes a hollow portion that is placed between a position in the vicinity of a wall surface of the intake duct and a position that the heat discharge plate is thermally bonded to the humidity detection element, and
   the hollow portion is a notch portion or an opening portion that blocks a heat transmission.

6. The measurement device according to claim 3, wherein
   the molded resin portion includes a contraction portion that is placed at a position of the molded resin portion closer to a wall surface of the intake duct than the humidity detection element, and
   the contraction portion has a dimension of at least one of a thickness or a width which is smaller than that of other parts of the molded resin portion.

7. The measurement device according to claim 2, wherein
   the circuit substrate and an electrical connection portion, which is made of a metal and is placed at a position in the vicinity of a wall surface of the intake duct, are electrically connected with each other through a signal wire of a heat resistor that blocks a heat transmission.

8. The measurement device according to claim 3, wherein
   the molded resin portion includes a window portion that directly introduces the intake air to a part of the humidity detection element, the measurement device further comprising:
   a metal plate arranged to cover at least a part of a periphery of the window portion in the molded resin portion.

9. The measurement device according to claim 2, wherein
   the heat discharge plate includes a width extension portion that is placed at a position where the heat discharge plate is thermally bonded to the humidity detection element, and
   the width extension portion has a width larger than that of other parts of the heat discharge plate.

10. The measurement device according to claim 2, wherein
    the heat discharge plate includes a heat discharge fin that is placed at a position to be directly in contact with the intake air so as to enlarge a surface where the heat discharge plate is in contact with the intake air.

11. The measurement device according to claim 2, further comprising:
    a plurality of via holes is placed at a position of the circuit substrate where the humidity detection element is mounted, the via holes penetrating the circuit substrate, and the via holes being filled with a metal.

12. The measurement device according to claim 2, wherein
    the heat discharge plate is tilted relative to a flowing direction of the intake air passing through the interior of the intake duct.

13. The measurement device according to claim 1, further comprising:
    a flowing amount sensor configured to measure a flowing amount of the intake air passing through the interior of the housing.

14. The measurement device according to claim 1, further comprising:
    an electrical connection portion configured to transmit a heat from the intake duct to the heat discharge portion.

15. The measurement device according to claim 1, wherein
    the heat discharge portion is configured to transmit a heat received from the intake duct to the intake air.

16. The measurement device according to claim 1, further comprising:
    a cover portion is configured to be fastened to the intake duct.

17. The measurement device according to claim 16, wherein
    the cover portion includes the connector for connecting an ECU.

18. The measurement device according to claim 17, wherein
    the electrical connection portion is a lead pin, and
    the electrical connection portion has a part exposed to an interior of the connector located at the cover portion.

19. The measurement device according to claim 1, wherein
    the electrical connection portion is located at a position in the vicinity of a wall surface of the intake duct.

20. The measurement device according to claim 1, further comprising:
    a molded resin portion that retains the humidity detection element, wherein the molded resin portion includes a contraction portion that is placed at a position of the molded resin portion closer to the connector than the humidity detection element is.

21. The measurement device according to claim 20, wherein the contraction portion has a dimension of a width which is smaller than that of other parts of the molded resin portion.

22. The measurement device according to claim 20, wherein the contraction portion has a dimension of a thickness which is smaller than that of other parts of the molded resin portion.

23. The measurement device according to claim 1, wherein the heat discharge portion includes a hollow portion that is placed at a position between the humidity detection element and the connector, and the hollow portion is a notch portion or an opening portion.

24. The measurement device according to claim 1, wherein at least a part of the electrical connection portion and the heat discharge portion is covered by resin.

25. The measurement device of claim 1, wherein a dividing portion between the heat discharge portion and the electrical connection portion is located further inward of an inner wall of the intake duct.

26. The measurement device of claim 1, wherein at least a portion of a surface of the humidity detection element is exposed from a molded resin portion that retains a part of the humidity detection element and the heat discharge plate.

* * * * *